United States Patent [19]

Akemi et al.

[11] Patent Number: 5,505,306

[45] Date of Patent: Apr. 9, 1996

[54] PACKAGE STRUCTURE OF DRUG-CONTAINING PRESSURE-SENSITIVE ADHESIVE SHEET

[75] Inventors: Hitoshi Akemi; Takashi Kinoshita; Takateru Muraoka; Kazuhiro Higashio; Saburo Otsuka, all of Osaka, Japan

[73] Assignee: Nitto Denko Corporation, Osaka, Japan

[21] Appl. No.: 274,162

[22] Filed: Jul. 14, 1994

[30] Foreign Application Priority Data

| Jul. 19, 1993 | [JP] | Japan | 5-177983 |
| Sep. 10, 1993 | [JP] | Japan | 5-249771 |
| Sep. 10, 1993 | [JP] | Japan | 5-249772 |

[51] Int. Cl.$^6$ .................................................. A61B 17/06
[52] U.S. Cl. .......................... 206/438; 206/440; 206/447
[58] Field of Search ................................. 206/438, 440, 206/447, 460, 484, 813

[56] References Cited

U.S. PATENT DOCUMENTS

| 2,974,787 | 3/1961 | Cooper | 206/438 |
| 3,616,156 | 10/1971 | Scholl | 206/440 |
| 5,115,913 | 5/1992 | Anhauser et al. | 206/447 |
| 5,384,174 | 1/1995 | Ward et al. | 206/440 |
| 5,423,737 | 6/1995 | Cartmell et al. | 206/440 |

FOREIGN PATENT DOCUMENTS

| 0423374 | 4/1991 | European Pat. Off. |
| 451782 | 12/1992 | Japan. |

*Primary Examiner*—David T. Fidei
*Attorney, Agent, or Firm*—Sughrue, Mion, Zinn, Macpeak & Seas

[57] ABSTRACT

A package structure, in which a drug-containing pressure-sensitive adhesive sheet comprising a support, a drug-containing pressure-sensitive adhesive layer, and a separator in this order is packaged and sealed in a packaging material, is disclosed, wherein unevenness is provided on at least one of the surface of the support on the side in contact with the inside of the packaging material, the surface of the separator on the side in contact with the inside of the packaging material, and the inside surface of the packaging material. The unevenness reduces the contact area between the packaging material and the sheet so that an adhesive, a plasticizer or any liquid component of the adhesive layer is prevented from adhering to the inside of the packaging material. Therefore, the sheet can easily be taken out of unit package on use.

11 Claims, 8 Drawing Sheets

PACKAGE STRUCTURE OF DRUG-CONTAINING PRESSURE-SENSITIVE ADHESIVE SHEET

FIELD OF THE INVENTION

The present invention relates to a package structure comprising a drug-containing pressure-sensitive adhesive sheet for percutaneously administering the drug, packaged with a packaging material.

BACKGROUND OF THE INVENTION

Percutaneous absorption has recently been adopted as a means for administering a drug into a living body, which comprises adhering a drug-containing pressure-sensitive adhesive sheet to a skin of a living body. The drug-containing pressure-sensitive adhesive sheet generally comprises a support made of a synthetic resin, such as polyester or polyethylene, having formed on one side thereof a pressure-sensitive adhesive layer containing a drug for percutaneous absorption, with the surface of the adhesive layer being covered with a separator. Such a drug-containing pressure-sensitive adhesive sheet is usually packaged with an individual packaging material impermeable to moisture so as to prevent volatilization of the drug contained therein and to prevent the influences of moisture on the drug.

In the case of individually packaging the drug-containing pressure-sensitive adhesive sheet as above, if the adhesive is squeezed out from the extremities of the sheet, the adhesive squeezed out adheres to the inside of the packaging material, making it difficult to take out the drug-containing pressure adhesive sheet from the packaged body.

Where the pressure-sensitive adhesive layer contains a plasticizer, a tackifier or a liquid component, there is a tendency that these substances ooze out from the extremities of the sheet, go around to the back of the support or separator, and adhere to the inside of the packaging material, and as a result, the drug-containing pressure-sensitive adhesive sheet is adhered to the inside of the packaging material, making it difficult to take out the sheet from the packaged body at the use thereof.

Further, in packaging the drug-containing pressure-sensitive adhesive sheet cut into a predetermined size, if the sheet cut are temporarily piled, a problem occurs that the slippability between the sheets deteriorates due to the squeeze-out of the pressure-sensitive adhesive or the go-around of the plasticizer as same as above, and the workablility of the packaging is greatly reduced.

In order to overcome these problems, it has been proposed to (1) use an oversized separator or (2) to provide projections serving as a spacer on the periphery of an oversized separator as disclosed in JP-B-U-4-51782 (the term "JP-B-U" as used herein means an "examined published Japanese utility model application").

According to method (1), the adhesive can be prevented from adhering to the inside of the packaging material and a plasticizer can be prevented from going around to the back of the separator. However, a problem still exists that the plasticizer, etc. tend to go around to the back of the support.

According to method (2), the projections serving as a spacer are effective to eliminate the problem of method (1). However, to use an oversized separator leads to an increased cost and a decreased yield, and special equipment is needed to provide projections on the periphery of the separator. Therefore, this method is not economical.

SUMMARY OF THE INVENTION

The present invention has been made to overcome the technical problems involved in the prior art.

Accordingly, an object of the present invention is to provide a package structure of a drug-containing pressure-sensitive adhesive sheet, in which the sheet does not adhere to the inside of a packaging material when the drug-containing pressure-sensitive adhesive sheet packaged with the packaging material is taken out of a packaged body, the drug-containing pressure-sensitive adhesive sheet can be taken out very easily at the use thereof, and decrease in yield, and increase in cost are not involved.

As a result of extensive study on a package structure for a drug-containing pressure-sensitive adhesive sheet comprising a support, a drug-containing pressure-sensitive adhesive layer, and a separator in this order, the inventors have found that the above object of the present invention is accomplished by forming unevenness on at least one of the surface of the support on the side in contact with the inside of a packaging material, the surface of the separator on the side in contact with the inside of a packaging material, and the inside surface of a packaging material. The unevenness reduces the substantial contact area between the sheet and the inside of the packaging material to thereby effectively prevent adhering of the sheet to the inside of the packaging material. The present invention has been completed based on this finding.

The package structure according to the present invention comprises a drug-containing pressure-sensitive adhesive sheet comprising a support, a drug-containing pressure-sensitive adhesive layer, and a separator in this order, packaged and sealed in a packaging material, wherein unevenness is provided on at least one of the surface of the support on the side in contact with the inside of the packaging material, the surface of the separator on the side in contact with the inside of the packaging material, and the inside surface of the packaging material.

DETAILED DESCRIPTION OF THE INVENTION

Figure 1:
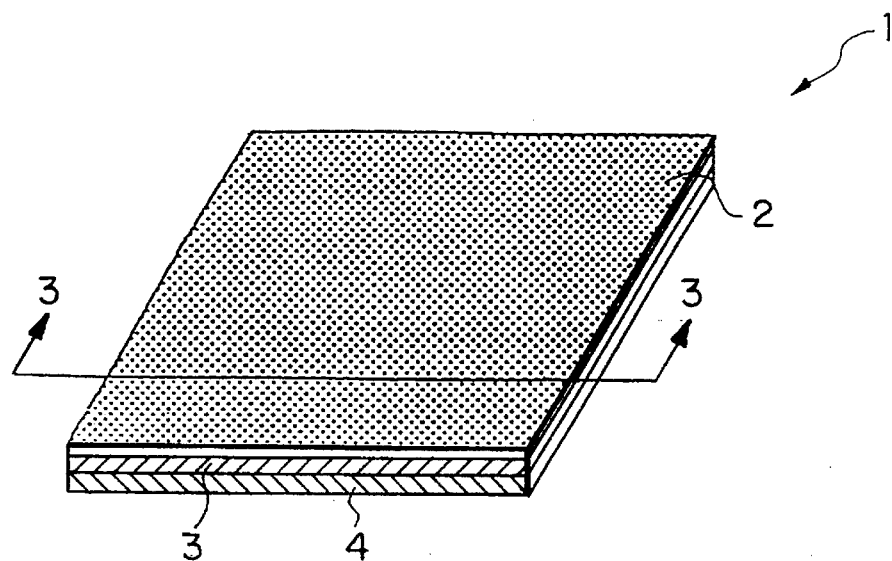
FIG. 1 is a perspective view of one example of the drug-containing pressure-sensitive adhesive sheet according to the present invention, seen from the side of the support.
Figure 2:
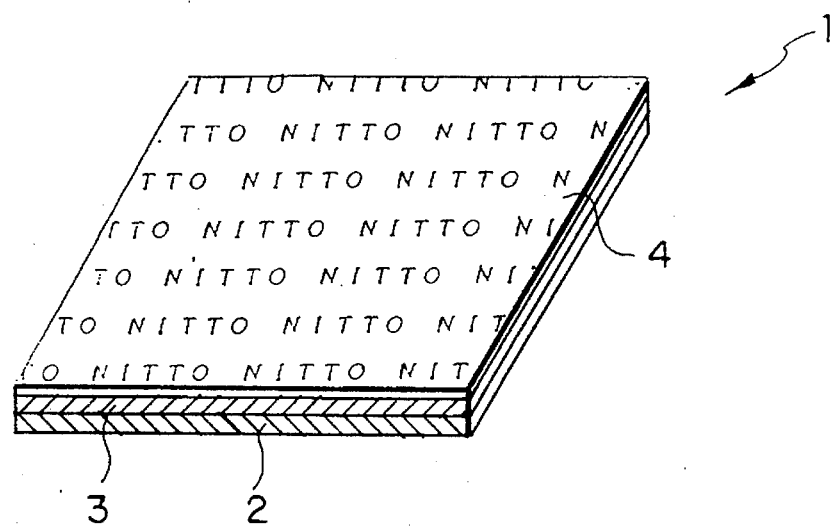
FIG. 2 is a perspective view of the drug-containing pressure-sensitive adhesive sheet of FIG. 1, seen from the side of the separator.

The drug-containing pressure-sensitive adhesive sheet according to the present invention (hereinafter sometimes referred to simply as "the sheet") comprises a support, a drug-containing pressure-sensitive adhesive layer (hereinafter sometimes referred to simply as "the adhesive layer") and a separator, formed in this order.

The support used in the present invention is not particularly limited in material so long as it is a sheet or a film made of various synthetic resins, nonwoven fabric, a metallic foil, etc., either in a single layer structure or in a multi-layer structure composed of some of these materials.

The adhesive layer comprises a pressure-sensitive adhesive containing therein any conventional drug which can be percutaneously absorbed in a body. Examples of the pressure-sensitive adhesive include which can be used are acrylic adhesives, rubber adhesives, silicone adhesives, vinyl ether adhesives, and so on. If desired, the adhesive layer may contain conventional additives, such as plasticizers, tackifiers, oily components, percutaneous absorption accelerators, fillers, and pigments.

The separator Which can be used includes a synthetic resin sheet or paper, the surface of which being subjected to a release treatment with a conventional release agent, such as a silicone resin or a fluorine-containing resin.

The package structure according to the present invention comprises the drug-containing pressure-sensitive adhesive sheet packaged and sealed in a packaging material.

The packaging material which can be used in the present invention is not particularly limited in material as long as it has a sheet or film form and is capable of enveloping the sheet. For achieving sealing package, heat-sealable materials, such as polyethylene, Surlyn (produced by E. I. du Pont de Nemours & Co.), an ethylene-vinyl acetate copolymer, an ethylene-vinyl alcohol copolymer, and Hightoron (produced by Tamapoly Corp.), are preferred. For prevention of volatilization of the drug contained in the sheet packaged or for prevention of moisture permeation, composite packaging materials prepared by laminating a polyester-based film or a metallic foil, such as an aluminum foil, on one surface of the heat-sealable film are preferably used. Packaging materials made of paper or nonwoven fabric can also be used where the drug is non-volatile or is insusceptible to decomposition with moisture.

The packaging material usually has a thickness of from about 10 to 200 μm.

The great characteristic of the package structure of the present invention is that at least one of the surface of the support on the side in contact with the inside of the packaging material, the surface of the separator on the side in contact with the inside of the packaging material, and the inside surface of the packaging material has unevenness.

The method for forming unevenness on these surfaces is not particularly limited. For example, surface unevenness can be formed by impressing using an engraved roller, etc. For example, a method can be employed that a roller or a press plate engraved with a desired pattern is pressed onto the surface to form the surface unevenness corresponding to the pattern. This method is very economical because a conventional apparatus can be used simply by making alteration on a roller or a press plate. Impression can also be conducted by general embossing.

The pattern engraved on a roller or a press plate preferably has rounded edges so as not to cause scratches or pin holes of the support, separator or packaging material.

Unevenness can also be formed by printing the surface with an ink comprising an expandable resin and then expanding the printed ink by, for example, heating. According to the printing method, the rate of expansion, i.e., the height of the unevenness can be controlled arbitrarily by selecting the kind and compounding proportion of a blowing agent.

It is also possible to form unevenness on the surface of a support, a separator or a packaging material by adhering particles or powder of an organic or inorganic substance thereto. Usable organic substance particles include those made of natural or synthetic materials. Synthetic materials are preferred on account of their stable quality. Examples of the synthetic materials include thermoplastic resins and thermosetting resins.

The particles or powder of natural or synthetic materials can be adhered by heat fusion or with a hot-melt adhesive or by fixing under pressure.

Unevenness may also be formed by subjecting the surface to sanding or by incorporating a matting agent into the material forming the support, separator or packaging material.

Unevenness may also be formed by laminating an unevenness-forming member. While not limiting, the unevenness-forming member used preferably includes woven or nonwoven fabric because of its cheapness. Woven or nonwoven fabric made of thermoplastic resins are particularly preferred because it is easily laminated by thermocompression bonding.

In the present invention, it is of importance to select a proper area proportion of the projections of the thus formed unevenness to the entire uneven surface of the support, separator or packaging material. Such a proper area proportion varies depending on the kind or composition of the adhesive used in the adhesive layer and cannot be generalized. However, the area proportion of the projections of at least one surface preferably ranges from 5 to 90%, and more preferably from 10 to 80%, based on the entire area of the surface on which unevenness is provided. If this area proportion is less than 5%, the effect of the projections as a spacer tends to be insufficient to reduce the contact area between the support or separator and the inside of the packaging material, resulting in difficulty in taking the sheet out of the package. On the other hand, if the area proportion exceeds 90%, meaning that the area proportion of the recesses is less than 10%, the effect of unevenness formation is lessened, tending to bear the same result as described above.

The projections practically have a pitch of from 0.1 to 20 mm, preferably from 0.5 to 10 mm, and a height of from 2 μm to 2 mm, preferably from 2 to 1000 μm, taking into consideration substantial reduction in contact area between the sheet and the packaging material, prevention of adhering, heat-sealability of the peripheral portions of the packaging material, and bulkiness of the unit packages. In particular, the height of the projections is an important factor to be considered. If it is less than 2 μm, the effect of preventing adhering of the sheet to the packaging material tends to be insubstantial. Projections having a height exceeding 2 mm, besides being difficult to form, tend to result in poor heat-sealability, high bulkiness, and increased cost.

According to the package structure of the present invention, the substantial contact area between a drug-containing pressure-sensitive adhesive sheet and the inside of a packaging material is reduced. That is, the area of the sheet adhering to the inside of the packaging material is reduced. As a result, the sheet can be taken out of the package with ease on use.

The present invention will now be illustrated in greater detail by referring to the accompanying drawings.

Figure 3:
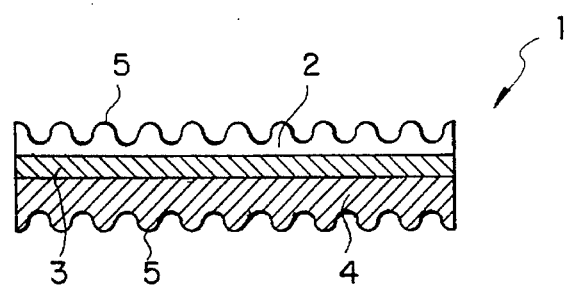
FIG. 3 is a cross section of the drug-containing pressure-sensitive adhesive sheet of FIG. 1 along X–X' line.
Figure 4:
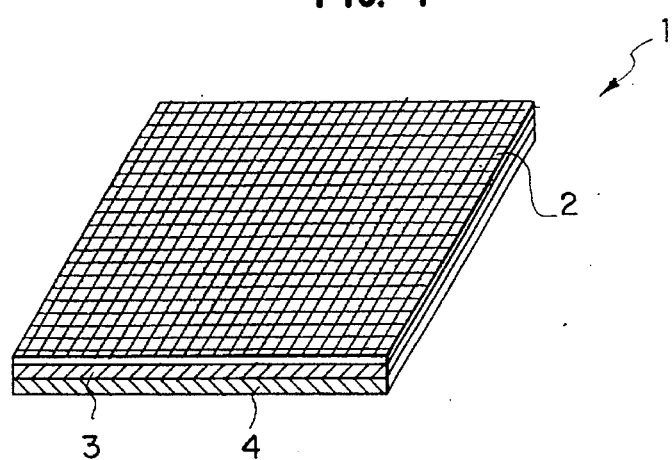
FIGS. 4 through 6 each is a perspective view of another example of the drug-containing pressure-sensitive adhesive sheet according to the present invention, seen from the side of the support.
Figure 5:
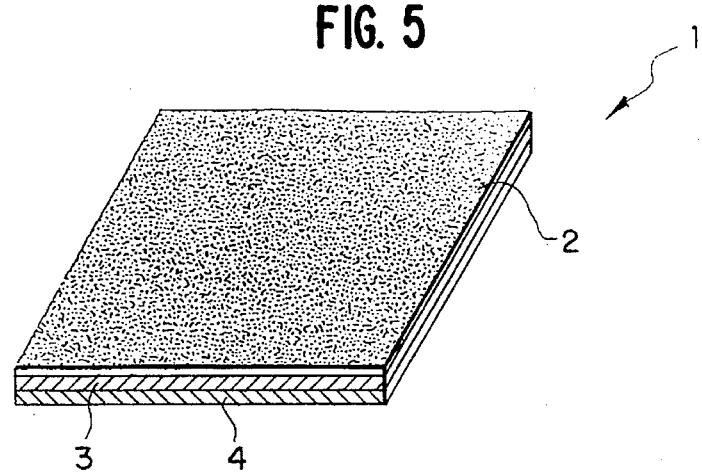
Figure 6:
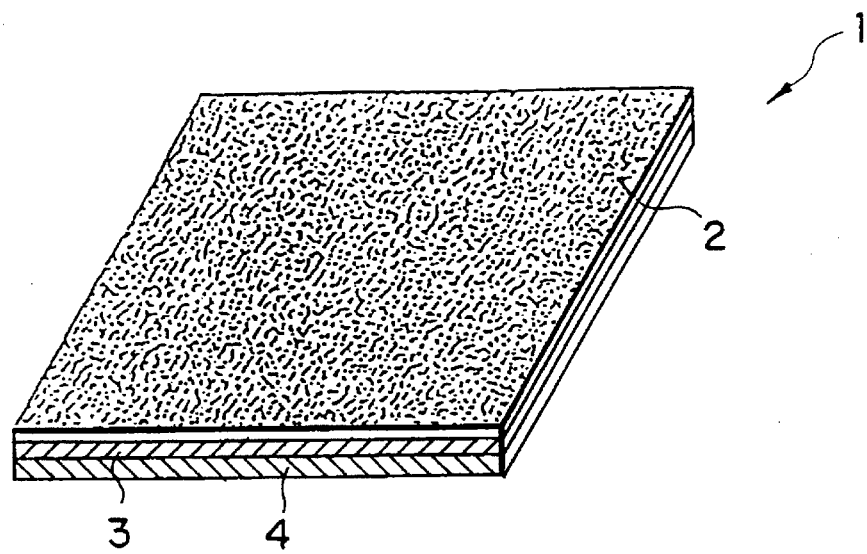
Figure 7:
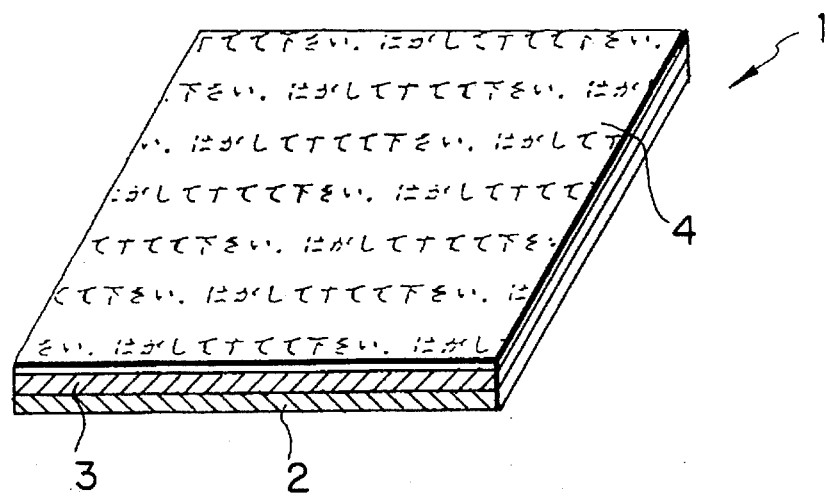
FIG. 7 is a perspective view of a still another example of the drug-containing pressure-sensitive adhesive sheet according to the present invention, seen from the side of the separator.

FIGS. 1 through 7 show examples of the drug-containing pressure-sensitive adhesive sheet according to the present invention, in which unevenness is provided on the surface of support 2 and/or separator 4. The sheet of FIGS. 1 (seen from support 2) and 2 (seen from separator 4) has unevenness formed on both support 2 and separator 4 by impression as shown in FIG. 3. The sheets of FIGS. 4, 5, and 6 has unevenness on support 2. The sheet of FIGS. 7 has unevenness on separator 4.

Unevenness on support 2 and/or separator 4 as shown in FIG. 3 can be formed by, for example, placing a support or a separator on a carrier having a smooth surface, such as a metal plate, and impressing an engraved roller or press plate thereon. This method can be carried out economically by using a conventional roller or press plate with necessary alteration.

Unevenness 5 may be given to both support 2 and separator 4 all at once by sandwiching previously prepared drug-containing pressure-adhesive sheet 1 between a pair of engraved rollers or press plates.

The shape or pattern of unevenness 5 is not limited and includes allover dots (FIG. 1), a repeating pattern of specific letters indicating the name of the manufacturer, instructions of use, etc. (FIGS. 2 and 7), a checkered pattern (FIG. 4), a fine particle pattern (FIG. 5), a matte pattern (FIG. 6), a wavy pattern (not shown), and a combination thereof.

Figure 8:
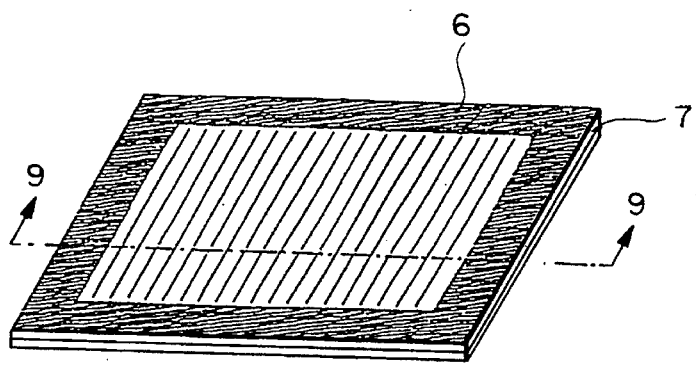
FIG. 8 is a perspective view of one example of the package structure according to the present invention.
Figure 9:
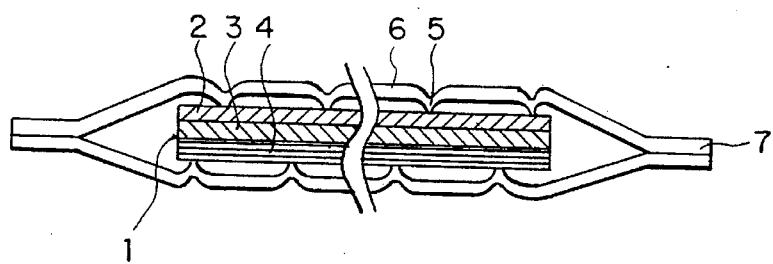
FIG. 9 is a cross section of the package structure of FIG. 8 along X–X' line.
Figure 10:
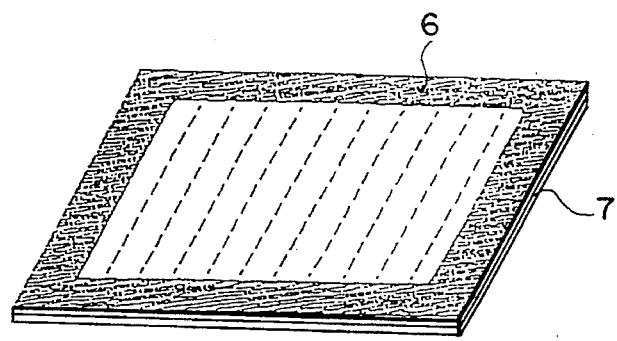
FIGS. 10 to 14 and 16 to 20 each is a perspective view of another example of the package structure according to the present invention.
Figure 11:
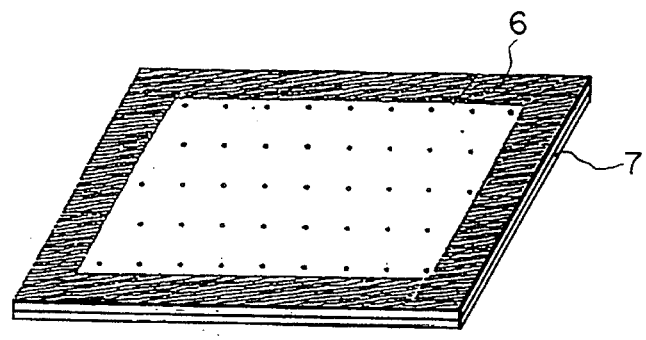
Figure 12:
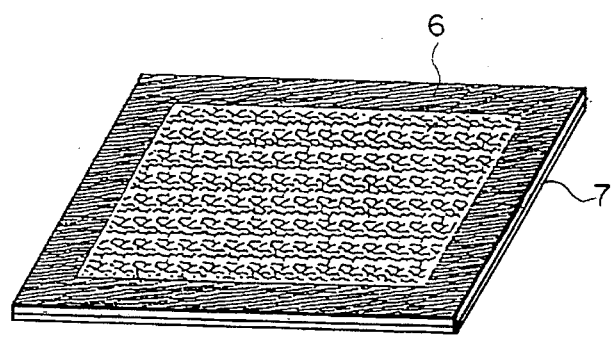

FIG. 8 and 9 show a perspective view and a cross section, respectively, of one example of the package structure according to the present invention, in which packaging material 6 has projections 5 on its inside surface.

FIGS. 10 through 13 show other package structures having projections on the inside of packaging material 6 similarly to FIG. 8.

Figure 13:
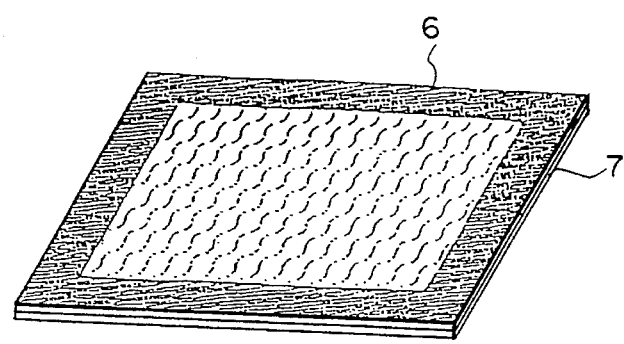

In these examples, the periphery 7 of packaging material 6 is heat-sealed for sealing sheet 1 therein, and unevenness 5 is formed on the inside of packaging material 6 by impression from the outer side thereof. The shape of unevenness 5 is not particularly limited and includes straight lines (FIG. 8), dotted lines (FIG. 10), dots (FIG. 11), a specifically designed pattern (FIG. 12), and wavy lines (FIG. 13).

Figure 14:
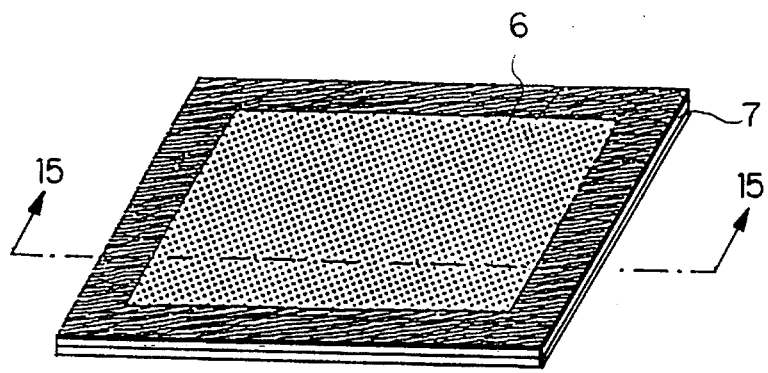
Figure 15:
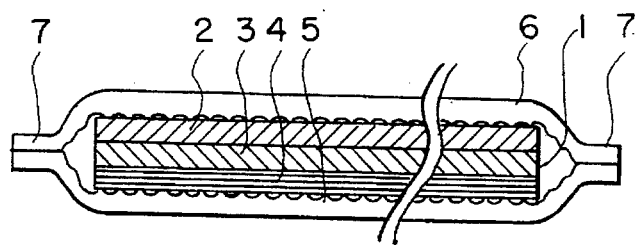
FIGS. 15 and 21 each is a cross section of the package structure of FIGS. 14 and 20, respectively, along the respective Y–Y' line.
Figure 16:
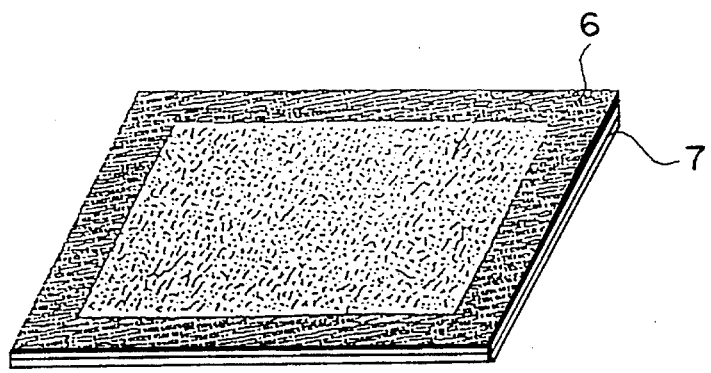
Figure 17:
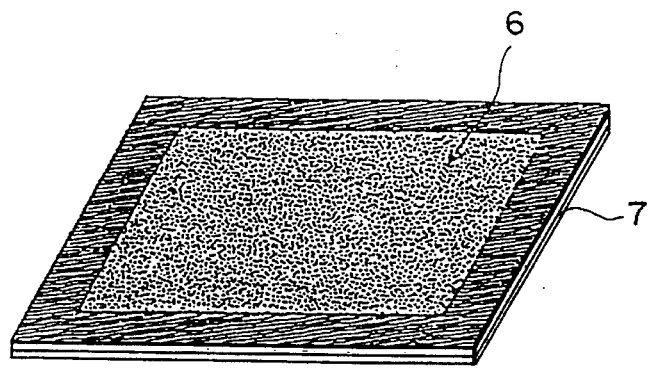
Figure 18:
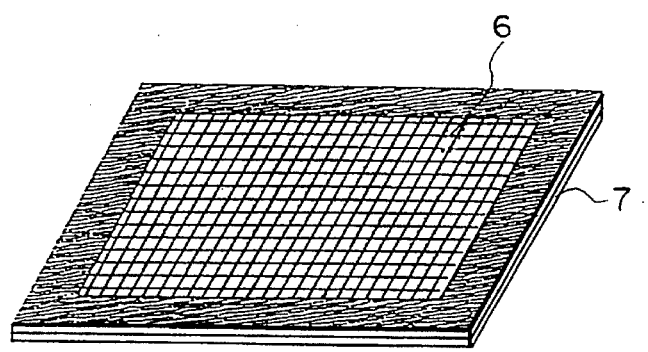
Figure 19:
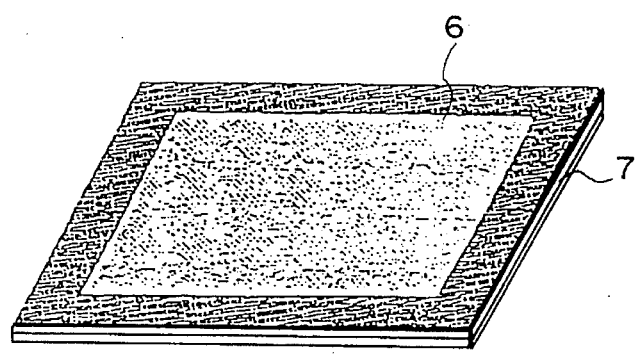

FIG. 14 illustrates another example of the package structure of the present invention, and FIG. 15 shows a cross section of the package structure of FIG. 14 along line Y–Y'. The package structure shown in FIGS. 14 and 15 is different from those shown in FIG. 8 and 9 in that unevenness 5 on the inside of packaging material 6 is formed by adhesion of fine particles in the former while in the latter the unevenness is formed by impression.

FIGS. 16 through 19 illustrate other examples of the package structure of the present invention.

The shape of unevenness 5 formed on packaging material 6 includes, in addition to those described above, a matte pattern (FIG. 16), a fine particle pattern (FIG. 17), a checkered pattern (FIG. 18), a repeating pattern of a specific design or letters (FIG. 19), and a combination of these patterns.

As is apparent from FIGS. 8 to 19, what is required for packaging material 6 is to have fine unevenness 5 on its inside surface. It does not matter whether or not the outside of the packaging material has such unevenness.

In packaging material 6 is packaged and sealed sheet 1, with the inside of packaging material 6 having point contacts or line contacts with support 2 or separator 4 of sheet 1.

With the inside of packaging material 6 having partial contacts with sheet 1, the adhesive, if pressed out, or any bleeding component, such as a plasticizer or a liquid component, is prevented from adhering to the inside of packaging material 6. Thus, sheet 1 can easily be taken out of the unit package on use.

The method for forming fine unevenness 5 on the inside of packaging material 6 is not particularly limited, and the same methods as used for support 2 or separator 4 apply. For example, unevenness can be provided by impression with, for example, an embossing roller.

Figure 20:
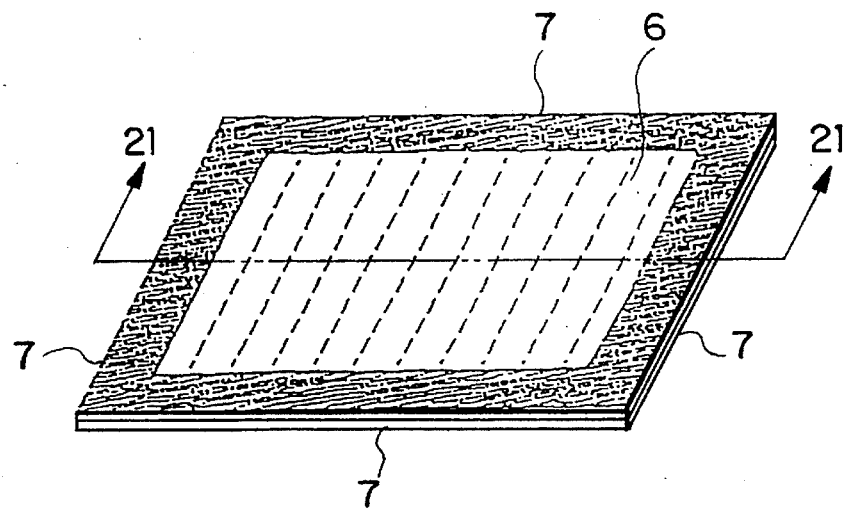
Figure 21:
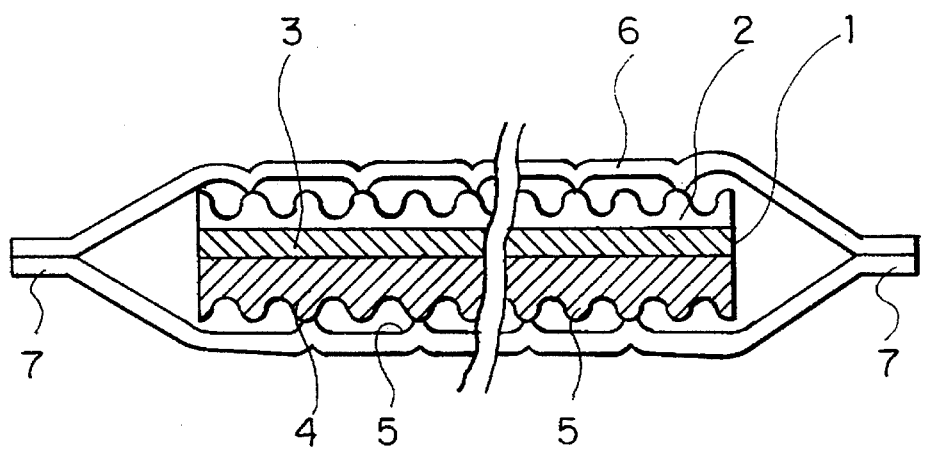

FIG. 20 illustrates a still another example of the package structure of the present invention, and FIG. 21 is a cross section thereof at Y–Y' line. It is seen from FIG. 21 that unevenness 5 is provided on the inside of packaging material 6 by impression from the outer side thereof and that unevenness 5 is also given to both sides of sheet 1, i.e., the surface of support 2 and the surface of separator 4. In this example, the substantial contact area between sheet 1 and packaging material 6 is further reduced so that sheet 1 can be taken out of the package more easily as compared with the above-described examples.

As described above, the present invention provides a package structure for a drug-containing pressure-sensitive adhesive sheet comprising a support, a drug-containing pressure-sensitive adhesive layer, and a separator in this order, in which the drug-containing pressure-sensitive adhesive sheet is packaged and sealed in a packaging material, wherein unevenness is provided on at least one of the surface of the support on the side in contact with the inside of the packaging material, the surface of the separator on the side in contact with the inside of the packaging material, and the inside surface of the packaging material. According to this structure, the substantial contact area between the sheet and the packaging material is reduced. That is, the area of the sheet adhering to the inside of the packaging material is reduced. Therefore, even where an adhesive is pressed out of the adhesive layer of the sheet or where a plasticizer or any liquid component oozes out of the adhesive layer, such a component hardly adheres to the inside of the packaging material, and the sheet can be taken out of the package with ease on use.

While the invention has been described in detail and with reference to specific examples thereof, it will be apparent to one skilled in the art that various changes and modifications can be made therein without departing from the spirit and scope thereof.

What is claimed is:

1. A package structure comprising a drug-containing pressure-sensitive adhesive sheet comprising a support, a drug-containing pressure-sensitive adhesive layer, and a separator, in this order, packaged and sealed in a packaging material, wherein unevenness is provided on at least one of the surface of said support on the side in contact with the inside of said packaging material, the surface of said separator on the side in contact with the inside of said packaging material, and the inside surface of said packaging material.

2. A package structure as claimed in claim 1, wherein said unevenness is formed by impression.

3. A package structure as claimed in claim 2, wherein said impression is conducted with an engraved roller.

4. A package structure as claimed in claim 1, wherein said unevenness is formed by printing.

5. A package structure as claimed in claim 4, wherein said unevenness is formed by printing with an ink comprising an expandable resin and expanding the printed ink.

6. A package structure as claimed in claim 1, wherein said unevenness is formed by adhesion of organic or inorganic particles or powder.

7. A package structure as claimed in claim 1, wherein said unevenness is formed by laminating an unevenness-forming member on the surface of said support, separator and/or packaging material.

8. A package structure as claimed in claim 7, wherein said unevenness-forming member is woven or nonwoven fabric.

9. A package structure as claimed in claim 1, wherein the area portion of projections of said unevenness formed on the support, separator and/or packaging material is from 5 to 90% based on the entire surface on which the unevenness is formed.

10. A package structure as claimed in claim 1, wherein the projections of said unevenness have a pitch of from 0.1 to 20 mm.

11. A package structure as claimed in claim 1, wherein the projections of said unevenness have a height of from 2 to 2,000 μm.

* * * * *